US00PP22984P2

(12) United States Plant Patent
Kerley et al.

(10) Patent No.: US PP22,984 P2
(45) Date of Patent: Aug. 21, 2012

(54) ***VIOLA* PLANT NAMED 'KERVIOMERI'**

(50) Latin Name: *Viola×wittrockiana*
Varietal Denomination: 'Kerviomeri'

(76) Inventors: David Kerley, Cambridge (GB); Priscilla Grace Kerley, Cambridge (GB); Timothy Edward Kerley, Cambridge (GB)

( * ) Notice: Subject to any disclaimer, the term of this patent is extended or adjusted under 35 U.S.C. 154(b) by 0 days.

(21) Appl. No.: 13/065,146

(22) Filed: Mar. 14, 2011

(51) Int. Cl.
*A01H 5/00* (2006.01)

(52) U.S. Cl. ..... Plt./323

(58) Field of Classification Search ..... Plt./323
See application file for complete search history.

*Primary Examiner* — Annette Para
(74) *Attorney, Agent, or Firm* — Cassandra Bright

(57) ABSTRACT

A new and distinct *Viola×wittrockiana* cultivar named 'KERVIOMERI' is disclosed, characterized by a unique combination of a large, round "pansy" type flower, found on a trailing plant. Flower color is a deep Violet-Blue color. Plants have a compact, trailing plant habit. The new variety is a *Viola×wittrockiana*, suitable for outdoor landscape and container use.

2 Drawing Sheets

Figure 1:
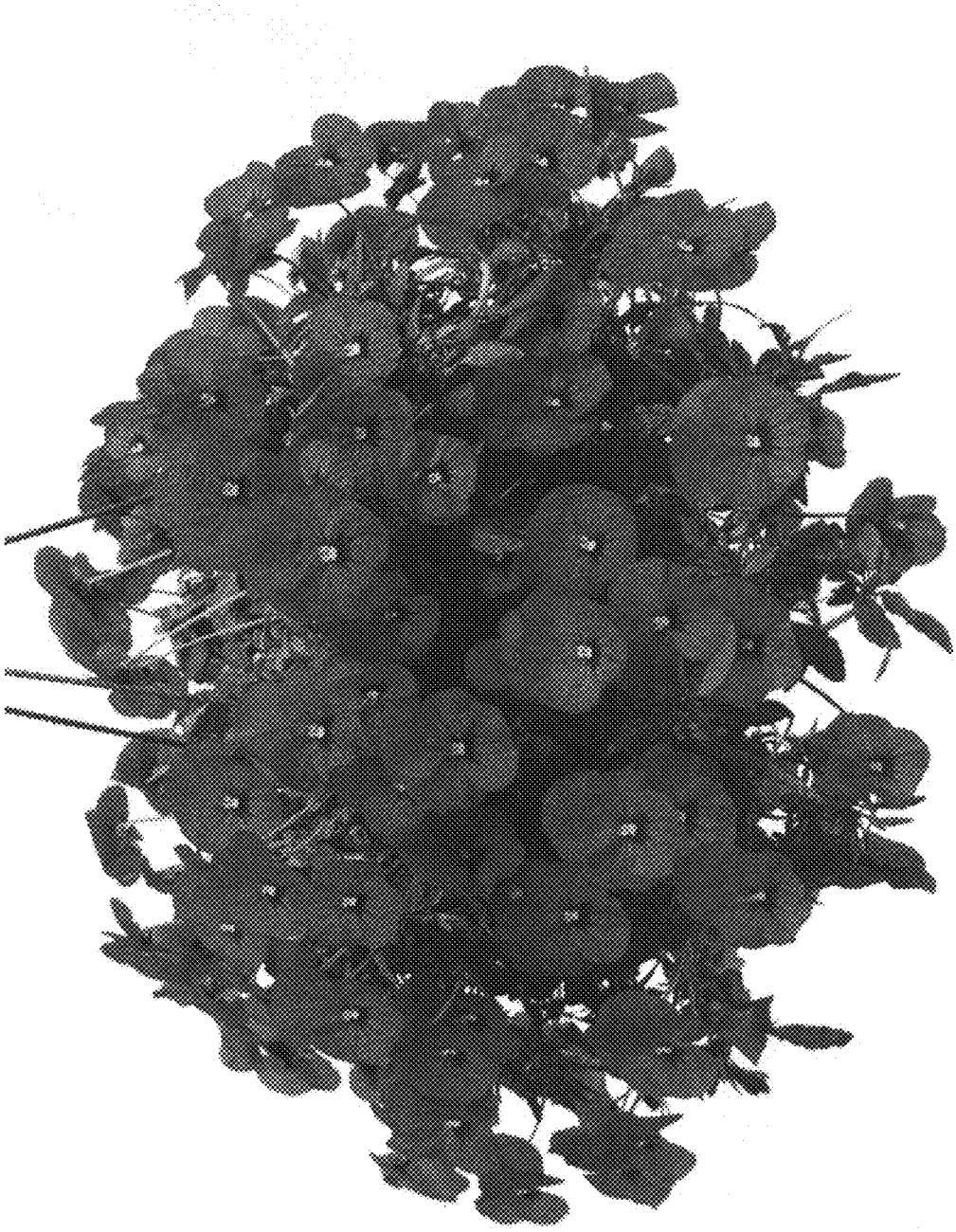

Latin name of the genus and species: *Viola×wittrockiana.*
Variety denomination: 'KERVIOMERI'.

BACKGROUND OF THE INVENTION

The new cultivar is the product of a planned breeding program under the direction of the inventors, David Kerley, Priscilla Kerley and Timothy Kerley, all citizens of the United Kingdom. The objective of the breeding program was to produce new trailing *Viola×wittrockiana* cultivars for commercial ornamental purposes. The new cultivar resulted from the crossing of two unpatented proprietary seedlings. The seed parent was referred to as '03-87-1' and the pollen parent was referred to as '03-88-1'. The cross resulting in 'KERVIOMERI' was performed during May of 2003. The selection of the new variety 'Kerviomeri' was made in April 2004, by the inventors at a research greenhouse located in Cambridge, UK.

Asexual reproduction of the new cultivar 'KERVIOMERI' by vegetative cuttings was first performed at the same research greenhouse in Cambridge, UK in July of 2004, and has shown that the unique features of this cultivar are stable and reproduced true to type in successive generations.

SUMMARY OF THE INVENTION

The cultivar 'KERVIOMERI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERVIOMERI' These characteristics in combination distinguish 'KERVIOMERI' as a new and distinct *Viola* cultivar:

1. Unique round "pansy" flower, on a trailing *Viola* plant, rather than the elongated flower form more commonly found on spreading or trailing types which are usually *Viola×williamsii.*
2. Large flower.
3. Spreading, trailing plant habit.

4. Exceptionally compact habit when grown in a small pot.
5. Deep Violet-Blue flower color.

PARENT COMPARISON

Plants of the new cultivar 'KERVIOMERI' are similar to plants of the seed parent variety, in most horticultural characteristics. However, plants of the new cultivar produce smaller flowers, of a more violet-blue, than blue color. Additionally, the new variety produces a plant with a more trailing habit than the seed parent.

Plants of the new cultivar 'KERVIOMERI' are similar to plants of the pollen parent variety, in most horticultural characteristics. However, plants of the new cultivar produce smaller flowers, of a more violet-blue, than purple color. Additionally, the new variety produces a plant with a more trailing habit than the pollen parent.

COMMERCIAL COMPARISON

Plants of the new cultivar 'KERVIOMERI' are similar to plants of the commercial variety known as *Viola* 'Sunviobu', U.S. Plant Pat. No. 17,676, in some horticultural characteristics. However, plants of the new cultivar 'KERVIOMERI' are consistently overall more compact than 'Sunviobu' with an overall more controlled growth habit more suitable for small commercial pots. Additionally, 'KERVIOMERI' produces a larger, rounder flower, of a darker blue, a shorter peduncle. Finally, foliage of 'KERVIOMERI' is larger than foliage of 'Sunviobu'.

Plants of 'KERVIOMERI' can also be compared to the commercial variety *Viola* 'Flovelbl' U.S. Plant Pat. No. 20,738. Plants are similar in most horticultural characteristics, however, 'KERVIOMERI' produces a larger flower, with a more trailing plant habit. Additionally, plants of 'KERVIOMERI' produce flowers of a deeper color.

BRIEF DESCRIPTION OF THE PHOTOGRAPHS

The accompanying photograph in FIG. 1 illustrates in full color typical plants of 'KERVIOMERI' grown in an unheated poly house in Cambridge, UK. Plants are approximately 35 weeks old shown in a 20 cm basket, 3 rooted cuttings were planted per pot.

Figure 2:
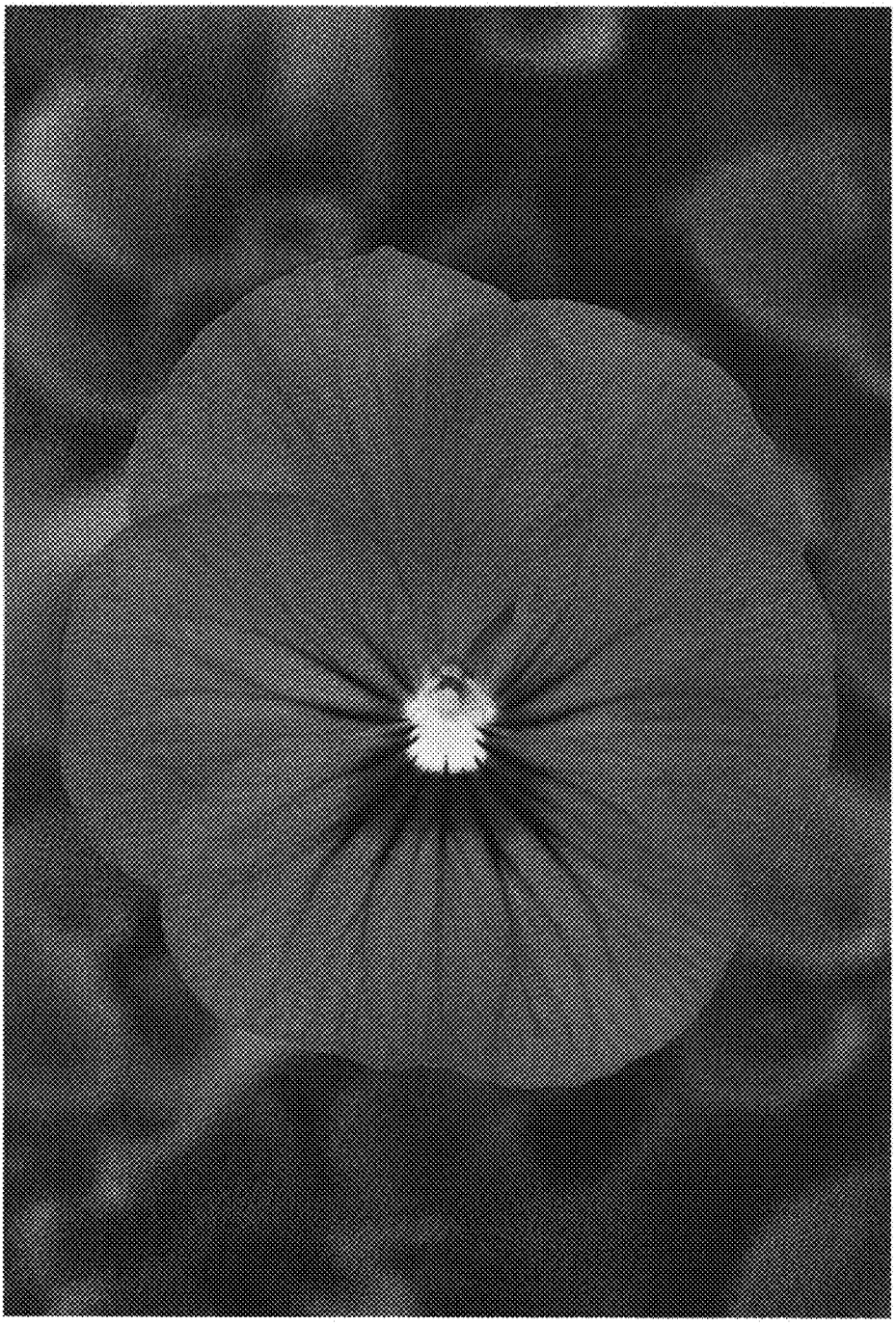

FIG. 2 illustrates a close up of a typical flower of 'KERVOIMERI'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 1995 except where general terms of ordinary dictionary significance are used. The following observations and measurements describe 'KERVIOMERI' plants grown in an unheated poly house in Cambridge, UK. The growing temperature ranged from approximately −5 to 12° C. at night to −2 to 18° C. during the day. 3 rooted cuttings were planted in a 20 cm basket. No chemical or photoperiodic treatments were given. Measurements and numerical values represent averages of typical flowering types.

Botanical classification: *Viola×wittrockiana* 'KERVIOMERI'.

Age of the plant described: Approximately 37 weeks, in a 20 cm basket.

PROPAGATION

Time to rooting: About 15 to 20 days at approximately 20° C.

Root description: Fine, fibrous.

PLANT

Growth habit: Spreading, trailing.
Height: Approximately 15 cm.
Plant spread: Approximately 60 cm.
Branching characteristics: Free branching.
Diameter of lateral branches: Approximately 0.6 cm.
Length of lateral branches: Approximately 27 cm.
Texture of lateral branches: Glabrous.
Internode length: Approximately 4 cm.
Strength of stem: Strong.
Color of lateral branches: Near RHS Yellow-Green 144A.
Quantity of lateral and sub lateral branches: Approximately 95.

FOLIAGE

Leaf:
- *Arrangement*.—Alternate.
- *Average length*.—Approximately 5.4 cm.
- *Average width*.—Approximately 2.2 cm.
- *Shape of blade*.—Obovate.
- *Apex*.—Rounded.
- *Base*.—Cordate.
- *Attachment*.—Petioled.
- *Margin*.—Crenulate.
- *Texture of top surface*.—Glabrous.
- *Texture of bottom surface*.—Glabrous.
- *Color*.—Developing foliage upper side: Near R.H.S. Green 137A. Developing foliage under side: Near R.H.S. Green 137C. Mature foliage upper side: Near R.H.S. Yellow-Green 147A. Mature foliage under side: Near R.H.S. Yellow-Green 147B.
- *Venation*.—Type: Pinnate. Venation color upper side: Near R.H.S. Green 137C. Venation color under side: Near R.H.S. Green 137D.

Petiole:
- *Length*.—3 cm.
- *Diameter*.—0.2 cm.
- *Color*.—Near RHS Yellow-Green 144A.

FLOWER

Bloom period: Naturally blooming March to November under United Kingdom outdoor conditions.

Inflorescence: Form: Single, axillary flowers, comprised of 5 petals total; 2 upper, 2 lateral and 1 lower in a single whorl.

Flower longevity on plant: About 5 days.

Persistent or self-cleaning: Self-Cleaning.

Fragance: None.

Flowers per plant: Approximately 125.

Flower bud:
- *Bud color*.—Near RHS Violet-Blue 94A.
- *Bud length*.—Approximately 2.2 cm.
- *Bud diameter*.—Approximately 0.9 cm.

Individual flower:
- *Flower size*.—Length: Approximately 6.4 cm. Width: Approximately 5.9 cm.

Petals:
- *Upper petals*.—Shape: Orbicular. Length: Approximately 3.5 cm. Width: Approximately 4.4 cm. Margin: Entire. Apex: Rounded.
  - *Color*.—When opening, upper surface: Near RHS Violet-Blue 89A. When opening, lower surface: Near RHS Violet-Blue 89D. Fully opened, upper surface: Near RHS Violet 87A, but darker. Fully opened, lower surface: Near RHS Violet 87D.
- *Lateral petals*.—Shape: Reniform. Length: Approximately 2.8 cm. Width: Approximately 3.3 cm. Margin: Entire. Apex: Rounded.
  - *Color*.—When opening, upper surface: Near RHS Violet-Blue 93A, 95C at base. When opening, lower surface: Near RHS Violet-Blue 96A, 96D at base. Fully opened, upper surface: Near RHS Violet 88A, 89D at base, Vein Blue 103A, 95C at base. Fully opened, lower surface: Near RHS Violet 88B, base near Violet-Blue 94B.
- *Lower petal*.—Shape: Very broad obocordate to orbicular. Length: Approximately 3.4 cm. Width: Approximately 4.3 cm. Margin: Entire. Apex: Rounded.
  - Color.—When opening, upper surface: Near RHS Violet-Blue 96A with 97B base, blotch 93B, vein Blue 102A, eye 14A. When opening, lower surface: Near RHS Violet-Blue 96C, with 97A towards base, lowermost base, Yellow 5C. Fully opened, upper surface: Near RHS Violet 88A, becoming Violet-Blue 89D towards Base. Vein Blue 103A, blotch Violet-Blue 93A, blotch approximately 7×14 mm. Eye Yellow 17A, eye approximately 5 mm×4 mm. Fully opened, lower surface: Near RHS Violet 88B, becoming Violet-Blue 94B towards base. Base Yellow 8A.

Additional flower data:
- *Spur on flower petal*.—Length: Approximately 0.5 cm. Width: Approximately 0.15 cm. Depth: Approximately 0.3 cm. Color: Near RHS Violet-Blue 97A.
- *Eye dimensions*.—Length: Approximately 0.5 cm. Width: Approximately 0.4 cm.

Sepals:

*Quantity*.—5.
*Arrangement*.—Whorled.
*Length*.—Approximately 2 cm.
*Width*.—Approximately 0.4 cm.
*Color*.—Near RHS Green 137C.
*Shape*.—Elliptic.
*Apex*.—Acute.
*Base*.—Obtuse.
*Texture*.—Glabrous.

Peduncle:

*Peduncle length*.—Approximately 13 cm.
*Peduncle diameter*.—Approximately 0.3 cm.
*Aspect*.—Upright with outward curve.
*Color*.—Near RHS Yellow-Green 144A.
*Texture*.—Glabrous.

REPRODUCTIVE ORGANS

*Stamen quantity*.—Approximately 5.
*Filament length*.—Approximately 0.1 cm.
*Anther length*.—Approximately 0.4 cm.
*Anther color*.—Near RHS Yellow-White 158B, tip Greyed-Orange 167A.
*Pollen color*.—Near RHS Yellow 10D.
*Pollen amount*.—Scant to moderate.
*Pistil length*.—Approximately 0.7 cm.
*Style length*.—Approximately 0.2 cm.
*Style color*.—Near RHS Yellow-Green 150D.
*Stigma shape*.—Bulbous with concave depression on uppermost portion.
*Ovary color*.—Near RHS Yellow-Green 150D.
*Stigma color*.—Near RHS Yellow-Green 151B.

OTHER CHARACTERISTICS

Disease resistance: Neither resistance nor susceptibility to diseases or pests has been observed in this variety.

Temperature tolerance: Tolerates high temperature to at least 35° C. Tolerates low temperatures to −10° C.

Fruit/seed production: Fruit and seed production not observed.

What is claimed is:

1. A new and distinct cultivar of *Viola* plant named 'KERVIOMERI' as herein illustrated and described.

* * * * *